United States Patent [19]

Ziskind

[11] 4,217,045
[45] Aug. 12, 1980

[54] CAPSULE FOR PHOTOGRAPHIC USE IN A WALLED ORGAN OF THE LIVING BODY

[76] Inventor: Stanley H. Ziskind, 1 Virunga Ct., Apt. B, Baltimore, Md. 21207

[21] Appl. No.: 127

[22] Filed: Dec. 29, 1978

[51] Int. Cl.$^2$ .................. A61B 1/06; G03B 15/02; G03B 29/00
[52] U.S. Cl. ................................. 354/62; 128/6; 354/126; 354/227
[58] Field of Search ............... 354/62, 63, 74, 75, 354/126, 227; 128/6-9, 11, 349 B, 349 BV; 350/91, 96.26, 293; 356/241

[56] References Cited

U.S. PATENT DOCUMENTS

| | | | |
|---|---|---|---|
| 1,828,141 | 10/1931 | Back | 128/8 |
| 2,641,977 | 6/1953 | Uji | 354/62 |
| 2,879,703 | 3/1959 | Blaise | 354/227 X |
| 3,100,482 | 8/1963 | Hett | 128/6 |
| 3,162,190 | 12/1964 | Del Gizzo | 126/6 |
| 3,221,593 | 12/1965 | Ferris | 356/241 |
| 3,511,147 | 5/1970 | Falenks | 354/62 |
| 3,791,377 | 2/1974 | Norby | 128/2 P |
| 4,038,977 | 8/1977 | Okada | 354/62 X |
| 4,040,413 | 8/1977 | Ohshiro | 128/6 |

FOREIGN PATENT DOCUMENTS

| | | | |
|---|---|---|---|
| 20880 | 12/1915 | Denmark | 354/63 |
| 135469 | 11/1902 | Fed. Rep. of Germany | 354/62 |
| 2428012 | 1/1976 | Fed. Rep. of Germany | 354/227 |

OTHER PUBLICATIONS

Martin Tobias, Internationl Handbook of Liquid Crystal Displays, 1975-1976, Second Edition with 1976 Supplement, sections 5.4.2, 5.4.3, Fig. 6-8.

*Primary Examiner*—John Gonzales
*Assistant Examiner*—Thomas H. Tarcza
*Attorney, Agent, or Firm*—John F. McClellan, Sr.

[57] ABSTRACT

A photographic capsule for diagnostic use in photographing a walled organ of the body such as a portion of the alimentary canal or the like includes a frame with a photographic unit and a balloon surrounding the photographic unit for expansion in place in the alimentary canal to smooth and space to a focal plane the walls of the portion to be photographed; the photographic unit making exposures through the balloon, illuminated by light relayed from outside the subject against a conical mirror through a fibre optics bundle within a shielding tube which also serves for retrieval, for holding signal leads, and as conduit for gas in inflating and deflating the balloon; in a preferred embodiment an electro-optical shutter is employed and a 360° view is provided by means of annular coaxial structure of photographic lens, shutter, film and balloon.

7 Claims, 3 Drawing Figures

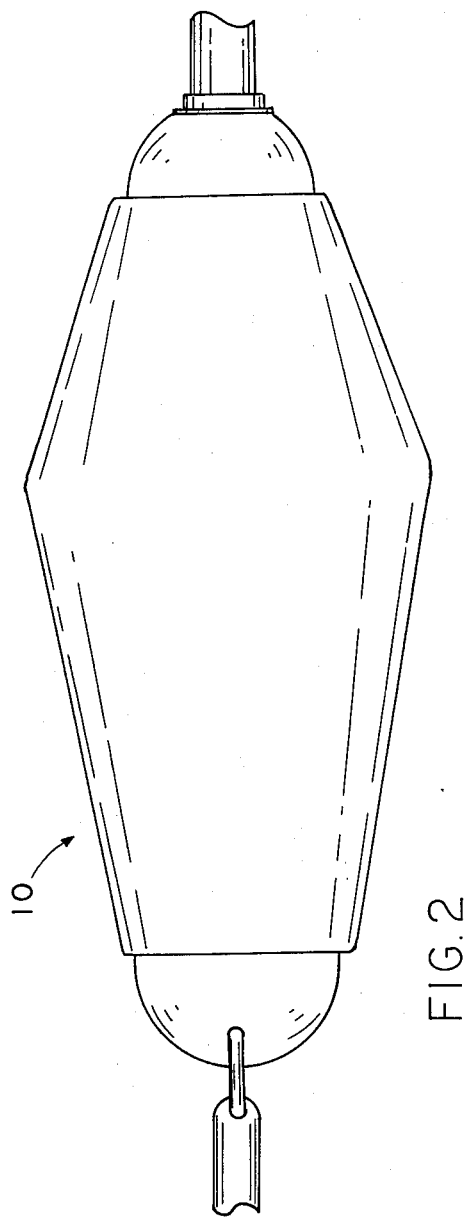
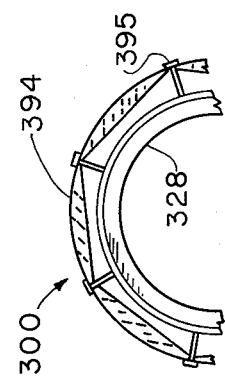
FIG. 2
FIG. 3

CAPSULE FOR PHOTOGRAPHIC USE IN A WALLED ORGAN OF THE LIVING BODY

This invention relates generally to medical apparatus and specifically to diagnostic equipment for internal use.

A principal object of the invention is to provide living-patient internal photographic information not before available to medical science with the same quality and speed.

Another object of the invention is to provide a capsule system for directly photographing sidewalls of many selected portions of the human alimentary canal such as the jejunum, ileum, esophagus, colon, stomach and duodenum, for example, and other structures such as the trachea.

Further objects are to provide a capsule system as described which unfolds and poses the sidewalls of such organs for optimum clarity of exposure, and which takes 360° photographs recording a band of the canal simultaneously.

Still further objects are to provide a capsule system as described which offers several modes of operation at the option of the practitioner using it, which is compact for easy insertion and retrieval and toleration by patients, and which gently expands and centers and aligns itself at the selected location within a patient, on command.

Yet further objects are to provide a capsule system as described which is easy to trace and to locate within patients, which is self-protective and patient-protective, which is generally failsafe, which is simple in construction, and economical to make and to use.

In the prior art various disclosures have been made of periscopic devices, including those of the following U.S. Pat. Nos.:

2,641,977 to Tatsuro Uji et al, June 16, 1953, is representative of a large number of long-shank camera endoscopes of various designs which are mentioned as capable of taking photographs of intestines;

3,221,593 to J. T. Ferris, Dec. 7, 1965, discloses a "borescope using a stepped cone reflector" and is stated to provide a 360° field of view. A transparent housing appears in the FIG. 4 embodiment.

3,791,377 to T. E. Norby et al, Feb. 12, 1974, discloses a swallowable probe or endoradiosonde representative of many of the type.

4,040,413 to Sasumu Oshior, Aug. 9, 1977, discloses an endoscope having a type of inflatable balloon structure on the exterior.

However, it is believed that none of the prior art devices supplies the combination of advantages of the present invention according to the present objects set forth.

In brief summary given for cursive description only and not as limitation, the invention includes a swallowable capsule having balloon structure for expanding and spacing a wall of the alimentary canal, and means for photographing the wall through the balloon structure.

The above and other objects and advantages of the present invention will become more readily understood on examination of the following description, including the drawings, in which like reference numerals refer to like parts:

FIG. 2 is a fragmentary view of the invention in collapsed configuration for insertion or removal; and FIG. 3 is a detail in partial section of a further embodiment.

Figure 1:
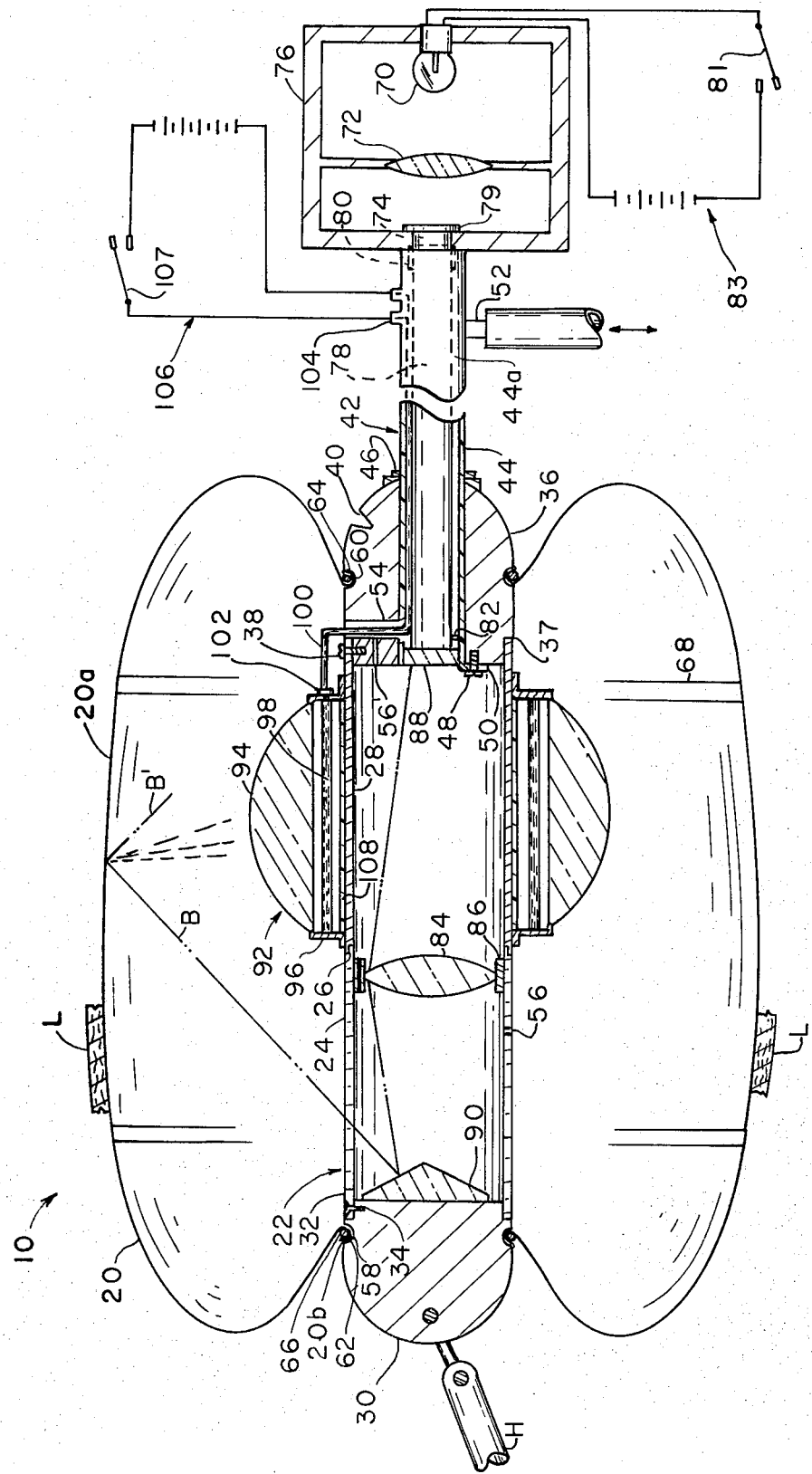
FIG. 1 is a side elevational detail in partial section showing the invention expanded in place in a part of an alimentary canal of a patient.

FIG. 1 illustrates an embodiment 10 of the invention in place in a portion of a human interior such as a small intestine, the lining L of which is posed for photographing by the invention as shown, and spaced from the photographic apparatus by provision of a special remotely inflatable/deflatable balloon 20 as an integral part of the invention. An exposure is made directly through the wall of the inflated balloon by the apparatus by following arrangement. It will be appreciated that the following description is, for the purposes of exposition, diagrammatical, and that the unit made be made even more compact and convenient without departing from the principles of the invention.

MAIN FRAME

The main frame 22 of the invention includes a cylindrical tube 24 preferably of any conventional lead glass which is transparent in the visible wavelengths but substantially opque to low level X-radiation, and affixed to this coaxially by a glass-to-metal seal 26 or any other conventional means is a cylindrical metal sleeve 28 which may be of any non-toxic, non-corrosive metal such as stainless steel. Frame and balloon are generally coaxial.

At the front end of the frame a convexly rounded-front plug 30 or end which may be of stainless steel closes the end of the glass cylinder, to which it may be affixed by any conventional means such as a glass-to-metal flange 32 on the cylinder engaged by screws 34 threaded into tapped holes in the plug.

At the rear, a rounded-back-end connector 36 which may be of stainless steel, connects as by a sliding, supportive overlap fit, with the stainless steel cylinder. It may be oriented to the cylinder about the long axis conventionally by a screw 38 extending radially into the cylinder and the periphery of the connector; thus it may be affixed detachably to the connector by other screws, also conventionally.

Orientation of the unit can be monitored by fluoroscopic observation of the orientation notch 40.

Insertion and retrieval means attaches to the connector and comprises a multi-purpose flexible cable assembly 42 including as an outer covering a smooth, strong, gas tight flexible tube 44 which may be polyethylene.

The interior or capsule end of this tube is cemented to the connector to form a gas tight overlap connection as at 46, and for additional security may be mechanically affixed to it, as by screws 48 on outturned flaps 50 of the tube within the connector, or by other conventional means.

BALLOON AND INFLATION

The outer or control end 44a of the tube is conventionally sealed by means to be discussed, and a side tube 52 near the outer end provides means for any medically acceptable, colorless inflating gas, which may be air, to be introduced under pressure, and withdrawn. The gas passes through the tube and out through a communicating vent 54 in connector 36 to the balloon interior, and preferably also at the same time from the interior of the tube into the interior of the main frame through one or more holes 56, 56' in it and the other structure.

The balloon 20 is molded preferably to have a relatively true semi-cylindrical periphery 20a when inflated. The ends have respective perforations 58, 60 with reinforcing flanging 20b of the same material as the balloon, one flanging fitting within peripheral groove 62 in the plug 30 and the other within the peripheral groove 64 in the connector 36.

A conventional tie 66 of nylon monofilament or the like may be wrapped around the flanging and tightly knotted, for greater security, while preserving easy changing of balloons.

Material for the balloon in this embodiment may be of composition such as surgical grade natural rubber, of thickness stretching to transparency when inflated, in one embodiment for 0.2 mm thickness this may be on inflation about 0.09 mm.

The balloon composition may include dark pigmentation to prevent fogging of the film by room light prior to insertion. As an example, a deep indigo coating of ink on the inside makes the balloon opaque when relaxed while not destroying substantial transparency to visible radiation when the balloon is inflated "Magic Marker" brand markers have been found to provide ink suitable for this. Focussing and centering the unit in situ are accomplishable by varying the pressure within the balloon as needed; this may be monitored by fluoroscope and by volume measurement of gas introduced.

If desired, as an option, a very light coating of a clear non-toxic grease (such as silicone grease) which does not attack natural rubber may be applied to the inner and outer surfaces to increase transparency.

Radio opaque stripes 68 which may be of metallic composition are painted in or otherwise provided for on the balloon periphery so that the position and degree of inflation can be monitored by fluoroscope.

ILLUMINATING AND PHOTOGRAPHING ELEMENTS

Lamp 70 and lenses 72 and 74 in housing 76 attached to the exterior end of the flexible cable diagrammatically represent any of many efficient commercially available sources, preferably of the cold light type, usable to project light along the frame interior through fibre-optics bundles, such as bundle 78 shown. This bundle is also typical of commerically available units used for analogous purposes. Control of exposure may be by a conventional shutter 79, or by a switch 81 in lamp-supply circuit 83.

The tube is made gas-tight around the exterior end of the bundle by cement 80, but in the remainder of the tube, the bundle is small enough in diameter to permit free passage of gas through the tube. The inner end of the bundle may be stabilized in position by spaced shims 82.

Lens 84, which may have a conventional ring 86 mounting it in slidably adjustable frictional engagement with the interior of cylindrical tube for focus. With or without a preferred diverging lens 88 at the end of the bundle, lens 84 relays the beam from the inner end of the bundle onto conical optical element or mirror 90, a portion which passes light to the tube exterior, and which mounts axially on the inner end of plug 30 by cement or other conventional means. The conical mirror then reflects the illumination in a 360° band around the system axis.

Angle of the conical mirror and position of the lens are conventionally made such as to locate the illuminated band around the periphery of photographic lens system 92, which may surround the illuminating lens as shown, when the balloon is at the full inflation diameter intended for a particular application.

It will be apparent from the incidence/reflection geometry that axially moving the illuminating lens and converging beam from it will vary the position of the illuminated band axially. Advantageously, as indicated by arrows in the ideal case shown, specular reflection $B_1$ of the illuminating beam B passes beyond the photographic lens system, which therefore can photograph more clearly by diffuse illumination, covering a 360° band around the photographic lens system.

Photograph lens system 92 comprises in this embodiment an annular or tubular lens 94, or photographic focussing means, which may be of simple cylindrical cross section but which for better optical performance may be of other conventional sectional configuration known in the art; borescope optics of the type may be used for the purpose. Here also lead glass is preferable to provide a degree of X-ray opacity. Cylindrical end-flanges 96 support the lens; these may be temporarily cemented to the steel tube of the main frame or may be pressed on it detachably.

An electro-optical shutter 98 in the form of a cylindrical member within the annular lens has insulated electrical control leads 100 (one shown) with conventional detachable plug connection 102 to it, passes loosely through the gas passageway 54 and then up the tube to emergence through cemented or otherwise sealed passage 104 through the tube wall and then to a typical control circuit repesented at 106 with switch 107. The space between the bundle and the tube for gas passage is made large enough to remain unblocked by these leads.

The electro-optical shutter may be of the liquid crystal type, the liquid contained in a glass or plastic walled annulus. For the liquid crystal a twisted-nematic type may be used, according to principles known and as an example, disclosed, in the "International Handbook Of Liquid Crystal Displays 1975–1976, Second Edition, with 1976 Supplement", Martin Tobias, published by Ovum Ltd. 14 Penn Road, London, N7 9RD England, (Library of Congress Call No. TK7882,.I6T6, 1876), in section 5.4.2 and in FIG. 5.6. And see U.S. Pat. No. 4,043,935. Alternatively, the DAP effect may be employed, as set out in the same publication in section 5.4.3 and the accompanying FIGS., 5.7 and 5.8, or the PECB effect may be employed as set out in section 5.4.4 of the publication.

Liquid crystal products for the purpose may be purchased from the Eastman Kodak Company, Rochester, N.Y., one pertinent catalog item being No. 11874. Another source of standard liquid crystal products for the purpose is Roche Chemical Division, Hoffman-La Roche Inc., Nutley, N.J. 07110. As will have been evident, the invention is not limited to electro-optical liquid crystal actuation of polarizing layers; thermal actuation is also possible according to known principles, and the balloon itself has a shutter capability in going from opaque to transparent on inflation.

The shutter and photographic lens are mounted concentric with and away from the film 108 which is wrapped around cylindrical frame member 28 and secured by elastic bands, cement or other conventional means. One or both end flanges 96 may be slid off for film loading.

FIG. 2 illustrates details of the invention 10 in balloon-collapsed configuration, the contours smoothed by the collapsed balloon. Actual size may be length about 2.5 cm and diameter about 9 to 12 mm; larger sizes may be employed.

OPERATION, FIRST EMBODIMENT

With the shutter protecting the film from ambient light (if Kerr cell type the shutter would be energized by applied potential) the capsule with balloon deflated is introduced, with, as an option, the aid of a conventional mercury weighted bag H pivoted by a ring to the front of the plug, as shown, if necessary, and conventionally positioned in the patient by swallowing, then the balloon is inflated, the position and inflation being monitored by fluoroscope and length of insertion.

The shutter is then de-energized and the light is turned on for an interval required for proper exposure of the film used. The shutter is re-energized and the capsule is withdrawn, taken to the darkroom, the balloon is removed and then the film (as by sliding it forward) and the film is developed.

FIG. 3 is a transverse sectional detail of a further embodiment 300 in which the 360° view is not continuous each element 394 of the lens (which may be held to tube 328 by any conventional means such as screws 395) being discrete to illustrate one possible arrangement other than the preferred embodiment. Illustrated also is the feature of having no shutter; the unit may be maintained in the dark to avoid fogging the film, and such can be done but is not always desirable.

In any embodiment a balloon may be employed as the film protecting component, entirely or in combination with a liquid crystal shutter if used, and of course with light switch and conventional shutter in any combination; similarly exposure times may be determined by appropriate combinations of these elements.

This invention is not to be construed as limited to the particular forms disclosed herein, since these are to be regarded as illustrative rather than restrictive. It is, therefore, to be understood that the invention may be practiced within the scope of the claims otherwise than as specifically described.

What is claimed and desired to be protected by United States Letters Patent is:

1. In a capsule for photographic use in a walled organ of the living human body and including a source of illumination, film and photographic focussing means, and means for retrieving the capsule from within the living human body, the improvement comprising: a frame, a balloon having attachment to the frame, means for inflating the balloon to press outward against the walls of said organ, means for photographing with one exposure a 360 degree field of view of the walls of said organ through the balloon, including the frame mounting the film and photographic focussing means within the balloon, a shutter, and said shutter coaxially mounted to the frame between the film and the photographic focussing means.

2. In a capsule as recited in claim 1, the shutter being a liquid crystal shutter.

3. In a capsule for photographic use in a walled organ of the living human body and including a source of illumination, film and photographic focussing means, and means for retrieving the capsule from within the living human body the improvement comprising: a frame, a balloon having attachment to the frame, means for inflating the balloon to press outward against the walls of said organ, means for photographing the walls of said organ through the balloon, including the frame mounting the film and photographic focussing means within the balloon with the photographic focussing means in an outward position relative to the film, the balloon wall being of a thickness and composition rendering at least a portion thereof substantially transparent to visible radiation on inflation, the frame having a tubular shape and the balloon attachment comprising affixation substantially coaxially thereover, the source of illumination including means for projecting light along the interior of the frame, means passing said light from the interior of the frame through the balloon at a position outward relative to the photographic focussing means, means exterior of the frame for controlling the source of illumination, the means for retrieving including means for controlling inflation and deflation of the balloon from a position sufficiently remote from the balloon to be outside a human body when the balloon is in a said walled organ of a said human body and comprising a flexible tube having communication with the interior of the balloon and means for detachable attachment to a source of compressed fluid, thereby comprising said means for controlling inflation and deflation, said means exterior of the frame including switching means for the source of illumination, fibre optics extending with said flexible tube to the frame from adjacent the source of illumination comprising said means for projecting, the means passing said light including the frame having a concentric transparent light-passing portion, and the means passing said light further including conical optical element reflecting means within the frame.

4. In a capsule as recited in claim 3, the frame having first and second ends of generally convexly rounded shape, and the means for retrieving having said communication through said first end.

5. In a capsule as recited in claim 4 the balloon affixation including respective detachable affixation at the first and at the second end.

6. In a capsule for photographic use in a walled organ of the living human body and including a source of illumination, film and photographic focussing means, and means for retrieving the capsule from within the living human body the improvement comprising: a frame, a balloon having attachment to the frame, means for inflating the balloon to press outward against the walls of said organ, and means for photographing the walls of said organ through the balloon, including the frame mounting the film and photographic focussing means within the balloon with the photographic focussing means in an outward position relative to the film, the balloon wall being of a thickness and composition rendering at least a portion thereof substantially transparent to visible radiation on inflation, the frame having a tubular shape and the balloon attachment comprising affixation substantially coaxially thereover, the photographic focussing means being coaxial with the frame, and a shutter coaxially mounted to the frame between the photographic focussing means and the film.

7. In a capsule as recited in claim 6, the shutter being a liquid crystal shutter.

* * * * *